US009682229B2

(12) United States Patent
Wu et al.

(10) Patent No.: US 9,682,229 B2
(45) Date of Patent: Jun. 20, 2017

(54) DRUG-ELUTING POLYMER COATED IMPLANTABLE ELECTRODE

(75) Inventors: Paul H. Wu, Edina, MN (US); Catherine E. Taylor, Fridley, MN (US); Terrel M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 800 days.

(21) Appl. No.: 13/537,249

(22) Filed: Jun. 29, 2012

(65) Prior Publication Data
US 2014/0005762 A1  Jan. 2, 2014

(51) Int. Cl.
*A61N 1/05* (2006.01)

(52) U.S. Cl.
CPC ........... *A61N 1/0568* (2013.01); *A61N 1/056* (2013.01); *Y10T 29/49194* (2015.01)

(58) Field of Classification Search
None
See application file for complete search history.

(56) References Cited

U.S. PATENT DOCUMENTS

| | | | |
|---|---|---|---|
| 6,115,625 A | 9/2000 | Heard et al. | |
| 7,041,308 B2 | 5/2006 | Shalaby et al. | |
| 8,088,404 B2 | 1/2012 | Udipi et al. | |
| 2004/0230298 A1 | 11/2004 | Udipi et al. | |
| 2005/0084515 A1 | 4/2005 | Udipi et al. | |
| 2007/0051531 A1* | 3/2007 | Borgaonkar et al. | 174/126.1 |
| 2009/0043378 A1 | 2/2009 | Cheng et al. | |
| 2011/0021899 A1* | 1/2011 | Arps | A61K 9/0009 600/372 |
| 2011/0087315 A1 | 4/2011 | Richardson-Burns et al. | |
| 2011/0112617 A1 | 5/2011 | Atanasoska et al. | |

FOREIGN PATENT DOCUMENTS

EP  2 274 995 A  8/1994
WO  WO 02/04062 A2  1/2002

OTHER PUBLICATIONS (PCT/US2013/047074) PCT Notification of Transmittal of the International Search Report and the Written Opinion of the International Searching Authority.
Cogan, "Neural Stimulation and Recording Electrodes," Annu. Rev. Biomed. Eng., 2008; 10:275-309.
Guimard et al., "Conducting Polymers in Biomedical Engineering," Prog. Polym. Sci., 2007 (32):876-921.
Habraken et al., "Introduction of Enzymatically Degradable Poly(trimethylene carbonate) Microspheres into an Injectable Calcium Phosphate Cement," Biomaterials, 2008; 29:2464-2476.

(Continued)

Primary Examiner — Erica Lee

(57) ABSTRACT

An electrode of an implantable medical lead is coated with a polymeric composition that includes (i) a terpolymer formed from monomer subunits consisting essentially of vinyl acetate, alkyl methyl acrylate and n-vinyl pyrrolidone; (ii) a copolymer formed from monomer subunits consisting essentially of vinyl acetate and alkyl methacrylate; and (iii) polyvinyl pyrrolidone. The coating does not substantially adversely affect impedance properties of the electrode.

20 Claims, 6 Drawing Sheets

(56) References Cited

OTHER PUBLICATIONS

Hezi-Yamit et al., "Impact of Polymer Hydrophilicity on Biocompatibility: Implication for DES Polymer Design," J. Biomed. Mater. Res. A, Jun. 2009; 90A(1):133-141.
Pai et al., "Electronic Structure and Properties of Alternating Donor-acceptor Conjugated Copolymers: 3,4-Ethylenedioxythiophene (EDOT) Copolymers and Model Compounds," Polymer, 2006; 47:699-708.
Udipi et al., "Development of a Novel Biocompatible Polymer System for Extended Drug Release in a Next-Generation Drug-eluting Stent," J. Biomed. Mater. Res. A, Jun. 15, 2008; 85(4):1064-1071.
Udipi et al., "The Next Generation Endeavor Resolute Stent: Role of the BioLinx™ Polymer System," EuroIntervention, 2007; 3:137-139.
Zhang et al., "Characterization of Flexible Neural Microelectrode Arrays Coated with Conducting Polymer PEDOT," 2nd International Conference on NeuroProsthetic Devices (ICNPD-2010), Beijing, China, Feb. 27-28, 2010. Abstract of oral presentation; 1 pg.
Zhang et al., "Polymer Photovoltaic Cells with Conducting Polymer Anodes," Advanced Materials, May 3, 2002; 14(9):662-665.

\* cited by examiner

DRUG-ELUTING POLYMER COATED IMPLANTABLE ELECTRODE

FIELD

The present disclosure relates to implantable medical devices; more particularly to implantable medical leads having electrodes coated with drug-eluting polymers.

BACKGROUND

Some currently available implantable medical leads, such as Medtronic, Inc.'s model 3830 leads, have electrodes that are coated with drugs, such as beclomethasone dipropionate (BDP). In some cases the drugs are coated; e.g. dipped or sprayed, directly on the electrodes after the leads have been built. Without polymer binder, the coating process can be challenging. For example, coating uniformity can be difficult to achieve. In addition, testing of the coating in these cases can be costly because testing must occur on an entire lead. Accordingly, if coating of the electrode does not meet manufacturing specifications, the entire lead is scrapped.

It would be desirable to coat the electrodes earlier in the manufacturing process so that the coating of the electrodes may be tested before incorporation into the leads. This would significantly reduce scrap costs because the electrode, as opposed to the entire lead, could be rejected if the coating did not meet specifications. However, because coatings of drugs applied directly to electrodes are not typically very durable, such direct coating is often not possible earlier in the manufacturing process.

One way to improve the durability and coating consistency of the drug is to incorporate the drug into a polymer matrix. However, many polymers are electrically insulating and thus would be functionally incompatible for coating of an electrode. Further, the biocompatibility of many electrically conductive polymers is not yet known. Selection of a polymer for coating of an electrode that is biocompatible and that does not significantly interfere with the electrical properties of the electrodes can be challenging.

One category of polymers that have been shown to be biocompatible and to have good drug elution properties are the polymer blends described in U.S. Pat. No. 8,088,404. The polymer blends described in U.S. Pat. No. 8,088,404 includes blends of a homopolymer, a copolymer and a terpolymer. The terpolymer comprises monomer subunits of vinyl acetate, alkyl methacrylate, and N-vinylpyrrolidone. The copolymer comprises monomer subunits of vinyl acetate and alkyl methacrylate. The homopolyer comprises polyvinyl pyrrolidinone. U.S. Pat. No. 8,088,404 discloses that such polymers, with an associated drug, may be used to coat implantable medical devices such as pacemaker leads. However, U.S. Pat. No. 8,088,404 does not disclose whether such polymers have suitable electrical properties for coating electrodes of such leads, and the chemical nature of suggests that they may be electrically insulating.

BRIEF SUMMARY

The present disclosure, among other things, describes implantable electrodes, leads and methods for coating electrodes with a drug in a polymer matrix. The polymer matrix is biocompatible and does not significantly interfere with, and may enhance, desired electrical characteristics or functioning of the electrode during use. In embodiments, the polymer matrix is a polymer blend described in U.S. Pat. No. 8,088,404, entitled BIOCOMPATIBLE CONTROLLED RELEASE COATINGS FOR MEDICAL DEVICES AND RELATED METHODS, published on Jan. 3, 2012, and naming Udipi et al. as inventors, which patent is hereby incorporated herein by reference in its entirety to the extent that it does not conflict with the present disclosure. A coating of Medtronic, Inc.'s BIOLINX™ biocompatible polymer, which is encompassed within the disclosure of U.S. Pat. No. 8,088,404, had not previously been characterized as being electrically conductive, but is described herein as not substantially interfering with, and slightly improving, certain electrical characteristics of electrodes.

In an embodiment described herein, an implantable medical lead includes (i) an electrode configured to contact tissue when implanted; (ii) a contact electrically coupled to the electrode, wherein the contact is configured to electrically couple the lead to a medical device; and (iii) a coating on the electrode, the coating comprising a polymer composition that includes (i) a terpolymer formed from monomer subunits consisting essentially of vinyl acetate, alkyl methyl acrylate and n-vinyl pyrrolidone; (ii) a copolymer formed from monomer subunits consisting essentially of vinyl acetate and alkyl methacrylate; and (iii) polyvinyl pyrrolidone. The coating does not substantially adversely affect impedance properties of the electrode.

In an embodiment described herein, a method includes (A) coating an electrode with a polymer composition comprising (i) a terpolymer formed from monomer subunits consisting essentially of vinyl acetate, alkyl methyl acrylate and n-vinyl pyrrolidone; (ii) a copolymer formed from monomer subunits consisting essentially of vinyl acetate and alkyl methacrylate; and (iii) polyvinyl pyrrolidone; and (B) incorporating the coated electrode into an implantable medical lead during assembly of the lead.

One or more embodiments of the devices, systems and methods described herein may provide one or more advantages over prior devices, systems and methods. Such advantages will be readily understood from the following detailed description when read in conjunction with the accompanying drawings.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

The present disclosure describes, among other things, implantable electrodes, leads and methods for coating electrodes with a drug in a polymer matrix. The polymer matrix is biocompatible and does not significantly interfere with, and may enhance, desired electrical characteristics or functioning of the electrode during use. In embodiments, the polymer matrix is a polymer blend described in U.S. Pat. No. 8,088,404, entitled BIOCOMPATIBLE CONTROLLED RELEASE COATINGS FOR MEDICAL DEVICES AND RELATED METHODS, published on Jan. 3, 2012, and naming Udipi et al. as inventors, which patent is hereby incorporated herein by reference in its entirety to the extent that it does not conflict with the present disclosure. A coating of Medtronic, Inc.'s BIOLINX® biocompatible polymer, which is described in U.S. Pat. No. 8,088,404, had not previously been characterized as being electrically conductive, but is described herein as not substantially interfering with, and slightly improving, certain electrical characteristics of electrodes.

Because of the presence of the polymer, therapeutic agents such as beclomethasone dipropionate may be coated on the electrode prior to the complete manufacture or assembly of the lead. Accordingly, if the coating is determined to not meet manufacturing standards, the electrode, rather than the entire lead, may be discarded.

The teaching presented herein are applicable to any suitable implantable medical lead, such as a lead configured to transmit electrical signals from a medical device to tissue of a patient via an electrode or a lead configured to transmit electrical signals from tissue of a patient to a medical device. Accordingly, the leads described herein may be therapeutic leads or monitoring leads. The leads may be employed with any suitable medical device, such as an active implantable medical device. Non-limiting examples of active implantable medical devices with which the leads described herein may be used include pacemakers, defibrillators, cardiac resynchronization therapy (CRT) devices, neurostimulators, gastric stimulators, cochlear implant devices, monitoring devices, and the like.

Figure 1:
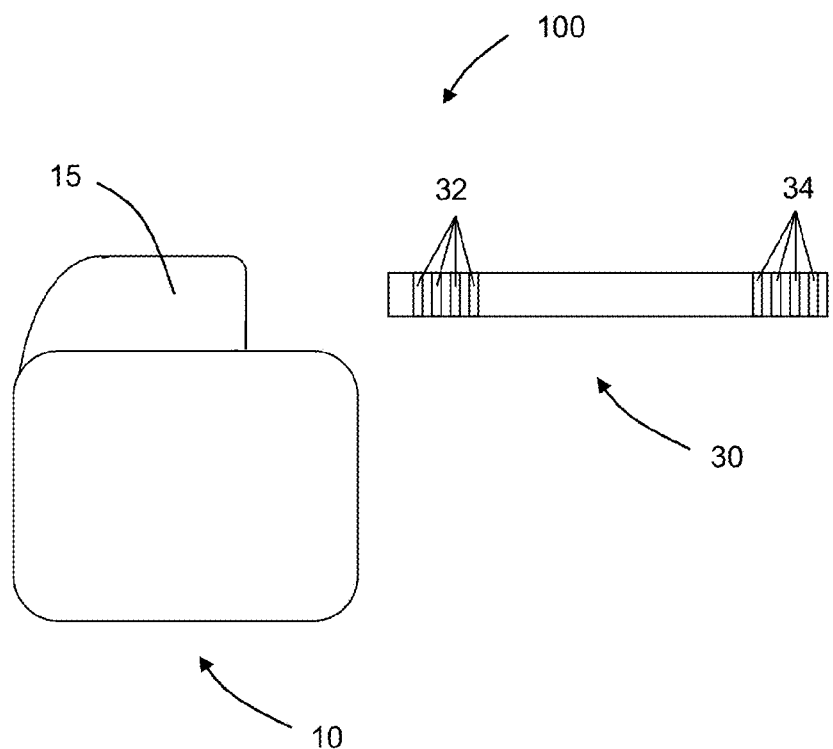
FIG. 1 is a schematic drawing of an embodiment of an implantable medical system including an implantable active medical device and a lead.

By way of example and with reference to FIG. 1, a schematic diagram of an implantable medical system 100 that includes a lead 30 is shown. The system 100 includes an active implantable medical device 10 and the lead 30. The depicted active device 10 includes a header 15 having one or more receptacles (not shown) for receiving proximal end of lead 30 such that internal contacts of the receptacle are configured to align with, and electrically couple to, contacts 32 disposed in proximity to the proximal end of the lead 30. The contacts 32 are electrically coupled to electrodes 34. Thus, when the lead 30 is properly inserted into the receptacles of the header 15 of the active device 10, electrical signals may be transmitted to or from the device 10 from or to the electrodes 34.

Figure 2:
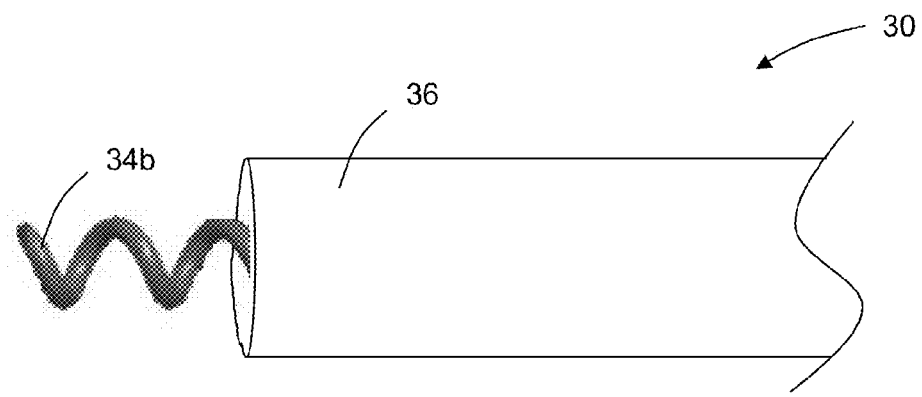
FIG. 2 is a schematic drawing of a distal portion of an embodiment of an implantable medical lead.

Referring now to FIG. 2, a distal portion of an embodiment of a lead 30 is shown. As depicted, embodiments of leads 30 described herein include a distal tip electrode 34b that extends from the distal end of the main lead body 36 and which are configured to penetrate into tissue of a patient (as opposed to being placed adjacent to a target tissue). In the depicted embodiment, the electrode 34b is a helix electrode configured to penetrate to anchor to target tissue. In embodiments where such tissue penetrating electrodes are employed, it may be preferable for the electrode to be coated with a releasable anti-inflammatory agent or a local anesthetic agent.

Figure 3:
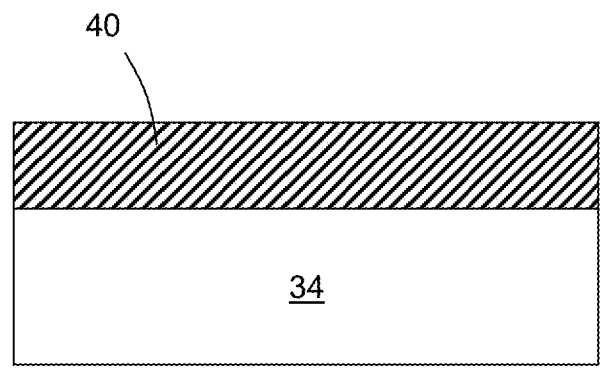
FIG. 3 is a schematic drawing of a cross-section of an embodiment of a coated electrode.

Referring now to FIG. 3, an electrode 34 having a coating 40 disposed thereon is shown. The coating 40 may be disposed on any portion or all surfaces of the electrode 34. Preferably, the coating does not substantially adversely affect the electrical characteristics of the electrode 34, such as impedance properties of the electrode. For example, the coating 40, in embodiments, does not increase impedance by more than 15% (relative to impedance measurements obtained with the same or a substantially similar electrode coated with BDP only—no polymer). In embodiments, the coating does not increase the impedance of the electrode by more than about 10% or more than about 5% (relative to impedance measurements obtained with the same or substantially similar electrode coated with BDP only—no polymer). In embodiments, the coating decreases the impedance of the electrode relative to impedance measurements obtained with the same or substantially similar electrode coated with BDP only—no polymer.

As described herein, it has been found that Medtronic, Inc.'s Biolinx® coating surprisingly decreased system impedance measurements when coated over the entire exposed surface (when incorporated into a lead) of the electrode (relative to an electrode coated with drug only—no polymer). Biolinx® is a polymer composition comprising a blend of a terpolymer, a homopolymer, and polyvinyl pyrrolidone. The terpolymer is formed from polymerizing a 25/27/48 (by weight) mixture of vinyl acetate, N-vinyl pyrrolidone, and n-hexyl methacrylate. The copolymer is formed by polymerizing a 60/40 (by weight) mixture of n-butyl methacrylate and vinyl acetate. The polymer composition includes 63% (by weight) of the terpolymer, 27% (by weight) of the copolymer, and 10% (by weight) of the polyvinylpyrrolidone.

It is believed that polymer compositions of a similar components or composition to the Biolinx® polymer blend will have similar effects with regard to electrical properties. That is, polymer compositions similar to the Biolinx® polymer blend should not substantially adversely affect the electrical properties of an electrode on which the polymer composition is coated.

In embodiments, an electrode is coated with a polymer or polymer blend having a composition as described in U.S. Pat. No. 8,088,404, the disclosure of which encompasses Biolinx® polymer blends and similar polymer compositions. As described in U.S. Pat. No. 8,088,404, the composition of the polymers and the polymer blend may be modified to control the release profile of a therapeutic agent associated with the polymer blend.

In embodiments, an electrode is coated with a polymer composition comprising a terpolymer, a copolymer and polyvinyl pyrrolidone. The terpolymer is formed from polymerization of vinyl acetate, alkyl methyl acrylate and n-vinyl pyrrolidone. The alkyl methyl acrylate may be selected from the group with the general formula of $C_nH_{2n+1}$, where n=1, 2, 3 to 18, such as methyl methacrylate, ethyl methacrylate, propyl methacrylate, butyl methacrylate, pentyl methacrylate, and hexyl methacrylate. The relative mole percent of the monomer subunits of the terpolymer comprises from about 2% to about 50% (e.g., from about 2% to about 30%, or from about 5% to about 30%) vinyl acetate, from about 20% to about 90% (e.g., from 40% to about 77%) alkyl methyl acrylate, and from about 10% to about 50% (e.g., from about 15% to about 30% or from about 18% to about 30%) n-vinyl pyrrolidone. The copolymer is formed from polymerization of vinyl acetate and alkyl methacrylate. The alkyl methyl acrylate may be selected from the group with the general formula of $C_nH_{2n+1}$, where n=1, 2, 3 to 18, such as methyl methacrylate, ethyl methacrylate, propyl methacrylate, butyl methacrylate, pentyl methacrylate, and hexyl methacrylate. The relative mole percent of the monomer subunits of the copolymer comprises from about 2% to about 90% (e.g., from about 2% to about 70%, of from about 5% to about 70%) vinyl acetate and from about 10% to about 98% (e.g., from about 30% to about 97%, or from about 30% to about 95%) alkyl methyl acrylate. The weight ratios of the terpolymer, homopolymer and polyvinyl pyrrolidone may be varied to any suitable degree. In embodiments, the polymer composition includes from about 40 to about 90 (e.g., from about 60 to about 70) weight percent of the terpolymer, from about 10 to about 50 (e.g., from about 20 to about 30) weight percent of the copolymer, and from about 2 to about 30 (e.g., from about 5 to about 15) weight percent of the polyvinyl pyrrolidone. In embodiments, the polymer composition comprises about 63 weight percent of the terpolymer, about 27 weight percent of the copolymer, and about 10 weight percent of the polyvinyl pyrrolidone In embodiments, a therapeutic agent is incorporated into the coating or polymeric composition of the coating for release upon implantation. As used herein, a therapeutic agent includes the therapeutic compound and pharmacologically acceptable salts, solvates, hydrates, isomers and polymorphs thereof Preferably, the therapeutic agent is released at a therapeutically effective concentration. In embodiments, one or more anti-inflammatory agents are incorporated into the polymeric composition. In embodiments, one or more anti-infective agents are incorporated into the polymeric composition. In embodiments, one or more local anesthetics are incorporated into the polymeric composition. In embodiments, one or more anti-hypertensive agents are incorporated into the polymeric composition. In embodiments, one or more therapeutic agents having different therapeutic functions (e.g., anti-inflammatory agents, anti-infective agents, local anesthetics, anti-hypertensive agent, etc.) are incorporated into the polymeric composition.

Any suitable anti-inflammatory agent may be incorporated into the coating. Non-limiting examples of anti-inflammatory agents include steroids, such as prednisone, dexamethasone, beclamethasone and methyl-prednisilone; and non-steroidal anti-inflammatory agents (NSAIDs). In embodiments, beclamethasone dipropionate is incorporated into the polymeric composition. One of ordinary skill in the art will recognize that other anti-inflammatory agents may be used.

Any suitable local anesthetic agent may be incorporated into the coating. Non-limiting examples of local anesthetics agents include lidocaine, prilocaine, mepivicaine, bupivicaine and articaine. One of ordinary skill in the art will recognize other local anesthetics that may be used.

Any suitable anti-infective agent may be incorporated into the coating. As used herein, "anti-infective agent" means an agent that kills or inhibits the growth of an infective organism, such as a microbe or a population of microbes. Anti-infective agents include antibiotics and antiseptics. Any suitable antibiotic may be used. As used herein, "antibiotic" means an antibacterial agent. The antibacterial agent may have bateriostatic or bacteriocidal activities. Non-limiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Non-limiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al., U.S. Pat. No. 4,642,104, which is herein incorporated by reference in its entirety to the extent that it does not conflict with the present disclosure, may be used. One of ordinary skill in the art will recognize other antibiotics that may be used.

In general, it is desirable that the selected antibiotic(s) kill or inhibit the growth of one or more bacteria that are associated with infection following surgical implantation of a medical device. Such bacteria are recognized by those of ordinary skill in the art and include *Stapholcoccus aureus, Staphlococcus epidermis*, and *Escherichia coli*. Preferably, the one or more antibiotics selected are effective against strains of bacteria that are resistant to one or more antibiotic.

To enhance the likelihood that bacteria will be killed or inhibited, it may be desirable to combine two or more antibiotics. It may also be desirable to combine one or more antibiotic with one or more antiseptic. It will be recognized by one of ordinary skill in the art that antimicrobial agents having different mechanisms of action or different spectrums of action may be most effective in achieving such an effect. In an embodiment, a combination of rifampin and micocycline is used. In an embodiment, a combination of rifampin and clindamycin is used.

Any suitable antiseptic may be included in the coating. As used herein, "antiseptic" means an agent capable of killing or inhibiting the growth of one or more of bacteria, fungi, or viruses. Antiseptic includes disinfectants. Non-limiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver-containing compounds (silver sulfadiazene, silver metal, silver ion, silver nitrate, silver acetate, silver protein, silver lactate, silver picrate, silver sulfate), and alcohols. One of ordinary skill in the art will recognize other antiseptics that may be employed in accordance with this disclosure.

It is desirable that the one or more antiseptic selected kill or inhibit the growth of one or more microbe that are associated with infection following surgical implantation of a medical device. Such microbes are recognized by those of ordinary skill in the art and include *Stapholcoccus aureus*, *Staphlococcus epidermis*, *Escherichia coli*, *Pseudomonus auruginosa*, and *Candidia*.

To enhance the likelihood that microbes will be killed or inhibited, it may be desirable to combine two or more antiseptics. It may also be desirable to combine one or more antiseptics with one or more antibiotics. It will be recognized by one of ordinary skill in the art that antimicrobial agents having different mechanisms of action or different spectrums of action may be most effective in achieving such an effect. In a particular embodiment, a combination of chlorohexidine and silver sulfadiazine is used.

Any suitable anti-hypertensive agent may be incorporated into the coating. Non-limiting examples of anti-hypertensive agents include diuretics, such as hydrochlorothiazide, chlorthalidone, or the like; sympatholytic agents such as clonidine, nadolol, pindolol, metaoprolol, or the like; vasodilators such as monoxidil, minoxididil N—O sulfate metabolites, or the like; and angiotension converting enzyme (ACE) inhibitors such as captopril, enalapril, lisinopril, losartan, or the like. One of ordinary skill in the art will recognize that other anti-hypertensive agents may be used.

The therapeutic agent may be present in the polymer composition at any suitable concentration. Preferably, the therapeutic agent is present in the polymer composition at a concentration sufficient to result in a therapeutic effect when released from the coating upon implantation of the electrode. In embodiments, the therapeutic agent is present in the polymer composition at a concentration from about 0.1% by weight to about 90% by weight. Preferably, the polymeric composition containing the therapeutic agent is homogenous.

A therapeutic agent may be incorporated into the polymer composition in any suitable manner. For example, the therapeutic agent can be covalently grafted to a polymer of the composition, either alone or with a surface graft polymer. Alternatively, the therapeutic agent may be coated onto the surface of the polymer either alone or intermixed with an overcoating polymer. The therapeutic agent may be physically blended with the polymer composition as in a solid-solid solution. The therapeutic agent may be impregnated into the polymer composition by swelling the polymer in a solution containing an appropriate solvent and the therapeutic agent. Any means of incorporating therapeutic agent into or on the polymeric composition may be used, provided that therapeutic agent may be released, leached or diffuse from the ultimate coating when the coating is contacted with bodily fluid or tissue.

In embodiments, the polymer composition and a therapeutic agent are intimately mixed either by blending or using a solvent in which they are both soluble. This mixture can then be coated onto a surface of the electrode or a primer layer. By way of example, one or more therapeutic agent may be added to a solvated polymer composition to form a therapeutic agent/polymer solution. The therapeutic agent/polymer solution can then be applied directly to electrode or primer layer; for example, by spraying (which includes electronanospraying) or dip coating, painting, dispensing on the electrode. As the solvent dries or evaporates, the therapeutic agent/polymer coating is deposited on the electrode. Furthermore, multiple applications can be used to ensure that the coating is generally uniform and a sufficient amount of therapeutic agent has been applied to the electrode.

A polymer composition, with or without associated therapeutic composition, as described herein may be applied to an electrode either directly or onto a polymer primer coat such a parylene or a parylene derivative. The coatings described herein can be applied to medical device surfaces, either primed or bare, in any suitable manner. Such applications methods include, but are not limited to, spraying, dipping, brushing, vacuum-deposition, and others. In embodiments, the coating is applied via electronanospraying. Electronanospraying employs electricity to disperse a liquid or fine aerosol, typically having particles with diametric dimensions of about 1 micrometer or less, which are then deposited onto a target; i.e., electrode. General discussion of techniques associated with electronanospray that may be used in connection with the teachings presented herein are disclosed in, e.g., (i) Salata, Oleg V., "Tools of Nanotechnology: Electrospray," *Current Nanoscience*, 1:25-33 (2005); and (ii) Gaskell, Simon J., "Electrospray: Principles and Practice," *J. Mass Spectrophotometry*, 32:677-688 (1997), which articles are hereby incorporated herein by reference in their respective entireties to the extent that they do not conflict with the disclosure presented herein.

Coatings consistent with the teaching of the present disclosure may be as thin as 1 micrometer or a thick as 1000 micrometers. It will be understood that the thickness of the coating may impact the electrical properties of the electrode on which the coating is applied. For example, if the coating is electrically insulating, thicker coatings may tend to results in increased impedance.

Figure 4:
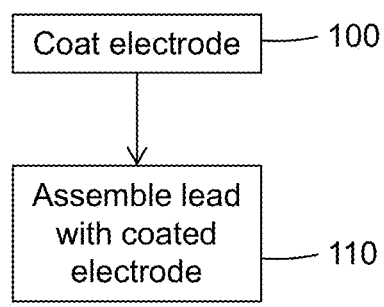
FIG. 4 is a flow diagram of an embodiment of a method.

Referring now to FIG. 4, an embodiment for a method of manufacturing a lead is depicted. The method includes coating an electrode (100) and assembling the lead with the coated electrode (110). As discussed above, such a method allows for the coating to be tested prior to assembly of the lead. Thus, if the coating does not meet manufacturing standards, the electrode (as opposed to the entire lead) may be scrapped.

Various embodiments of electrodes, leads, devices, systems and methods are described herein. Various aspects of some of the electrodes, leads, devices, systems and methods are summarized below.

In a $1^{st}$ aspect, an implantable medical lead comprises (i) an electrode configured to contact tissue when implanted; (ii) a contact electrically coupled to the electrode, wherein the contact is configured to electrically couple the lead to a medical device; and (iii) a coating on the electrode, the coating comprising a polymer composition that includes (i) a terpolymer formed from monomer subunits consisting essentially of vinyl acetate, alkyl methyl acrylate and n-vinyl pyrrolidone; (ii) a copolymer formed from monomer subunits consisting essentially of vinyl acetate and alkyl methacrylate; and (iii) polyvinyl pyrrolidone, wherein the coating does not substantially adversely affect impedance properties of the electrode.

A $2^{nd}$ aspect is a lead according to the $1^{st}$ aspect, wherein the polymer composition comprises from about 60 to about 70 weight percent of the terpolymer, from about 20 to about 30 weight percent of the copolymer, and from about 5 to about 15 weigh percent of the polyvinyl pyrrolidone.

A third aspect is a lead according to the first aspect, wherein the polymer composition comprises about 63 weight percent of the terpolymer, about 27 weight percent of the copolymer, and about 10 weight percent of the polyvinyl pyrrolidone.

A fourth aspect is a lead according to any of the first three aspects, wherein the relative mole percent of the monomer subunits of the terpolymer comprises from about 2% to about 30% vinyl acetate, from about 40% to about 77% alkyl methyl acrylate, and from about 15% to about 30% n-vinyl pyrrolidone.

A fifth aspect is a lead according to any of the first four aspects, wherein the relative mole percent of the monomer subunits of the copolymer comprises from about 2% to about 70% vinyl acetate and from about 30% to about 97% alkyl methyl acrylate.

A sixth aspect is a lead according to any of the first five aspects, wherein the alkyl methacrylate of the terpolymer and the alkyl methacrylate of the copolymer are independently selected from the group consisting of methyl methacrylate, ethyl methacrylate, propyl methacrylate, butyl methacrylate, pentyl methacrylate, and hexyl methacrylate.

A seventh aspect is a lead according to any of the first six aspects, wherein the alkyl methacrylate of the terpolymer is n-hexyl methacrylate and wherein the alkyl methacrylate of the copolymer is n-butyl methacrylate.

An eighth aspect is a lead according to any of the first seven aspects, wherein the coating further comprises a therapeutic agent.

A ninth aspect is a lead according to the eighth aspect, wherein the therapeutic agent is selected from the group consisting of an anti-inflammatory agent and an antimicrobial agent.

A tenth aspect is a lead according to the eighth aspect, wherein the therapeutic agent is an anti-inflammatory agent.

An eleventh aspect is a lead according to the eighth aspect, wherein the therapeutic agent is a steroid.

A twelfth aspect is a lead according to the eighth aspect, wherein the therapeutic agent is beclomethasone or a pharmaceutically acceptable salt thereof.

A thirteenth aspect is a lead according to the eighth aspect, wherein the therapeutic agent is beclomethasone dipropionate.

A fourteenth aspect is a lead according to any of the first thirteen aspects, wherein the electrode is an electrode configured to penetrate the tissue.

A fifteenth aspect is a lead according to any of the first fourteen aspect, wherein the electrode is a helix electrode.

A sixteenth aspect is a lead according to any of the first fifteen aspects, wherein the coating (i) does not increase the impedance of the electrode more than 10% relative to an uncoated electrode, (ii) does not increase the impedance of the electrode more than 10% relative to the same or substantially similar electrode coated with BDP alone, (iii) or does not increase the impedance of the electrode more than 10% relative to a helix tip electrode of a Medtronic, Inc. SELECT-SECURE Model 3830 lead in which the helix tip electrode is dip coated with BDP (no polymer).

A seventeenth aspect is a lead according to any of the first fifteen aspects, wherein the coating decreases the impedance of the electrode relative to an uncoated electrode.

An eighteenth is an implantable medical system comprising a lead according to any of the first seventeen aspects and an active medical device to which the lead is configured to operably couple.

A nineteenth aspect is a method comprising (A) coating an electrode with a polymer composition comprising (i) a terpolymer formed from monomer subunits consisting essentially of vinyl acetate, alkyl methyl acrylate and n-vinyl pyrrolidone; (ii) a copolymer formed from monomer subunits consisting essentially of vinyl acetate and alkyl methacrylate; and (iii) polyvinyl pyrrolidone' and (B) incorporating the coated electrode into an implantable medical lead during assembly of the lead.

A $20^{th}$ aspect is a method according to the $19^{th}$ aspect, coating the electrode comprises electro-nono-spraying the electrode with the polymer composition.

A $21^{st}$ aspect is a method according to the $19^{th}$ or $20^{th}$ aspect, further comprising incorporating a therapeutic agent into the polymer composition.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

As used herein "polymer subunit" or "subunit" refers to the polymer's individual molecular building blocks. In homopolymers the subunits are identical monomers such as polyethylene or polystyrene. However, copolymers can have numerous possible configurations. Co-polymers are the simplest copolymer and will be used in the following example. Co-polymers are composed of two dissimilar subunits. The subunits can be separate monomers, or oligomers. For example, a co-polymer having monomeric subunits is composed of two monomers such as ethylene (E) and styrene (S). The polymer chain can be random (for example, DNA and polypeptides are quintessential random polymers), non-random, blocked or segmented. In random co-polymers, as the name implies, there is no defined order to the monomer sequence, for example --EESESSEESSES-- (of course reaction kinetics may favor one coupling reaction over another; these examples are merely for illustrative purposes). Non-random co-polymers would have an alternating configuration such as ---ESESESESESESESES--. Block copolymers have a high number of covalently bonded repeat subunits such as -EEEEEEEESSSSSSSSSEEEEEEEEE--(ABA configuration) or -EEEEEEEEEESSSSSSSSSSS--(an ABn configuration). Finally, segmented co-polymers have a small number of repeat subunits such as --EESSEESSEESS-. If a third polymer is added, a terpolymer results. For example, say acrylic acid is added (A). A random terpolymer would look like --AAESASSEAEESAAESEASEASEA--. A non-random terpolymer would look like --ASEASEASEASE-ASEASEASE--. And a block terpolymer may look like this --AAASSSEEEAAASSSEEEAAASSSEEE--. There are myriad other possible configurations depending on the number of monomeric subunits involved. Still more complex copolymers are possible when the subunits are polymers themselves (oligomeric subunits). Copolymer and terpolymers composed of oligomeric subunits often resemble random and block polymers in their behavior and therefore will not be considered further. Finally, this brief description of polymer primary structure (the chain makeup) did not consider graft polymers (where monomer and polymer side chains are attached as pendent groups to the primary polymer chain) or crosslinking between chains and/or pendent groups (secondary polymer structure). However, any and all of the primary and secondary structures discussed herein and variations thereon are considered within the scope of the present invention.

As used herein, "impedance properties" of an electrode refers to impedance values obtained for the electrode when measured in a system including a second reference electrode. By way of example, unipolar impedance values of a test electrode of an implantable medical lead may be measured between the test electrode and an indifferent electrode in a salt solution tank at a controlled temperature. Impedance values obtained for the system are used herein to refer to "impedance properties" of the electrode. As used herein, "impedance of an electrode" and "impedance properties of an electrode" are used interchangeably and have the meaning ascribed to "impedance properties of the electrode."

As used herein, "significantly adversely affecting" impedance properties of an electrode, "significantly adversely affect" impedance properties of an electrode, or the like, means decreasing the impedance properties of the electrode to a level that renders the electrode unsuitable for clinical application. It will be understood that an increase in impedance of an electrode can be somewhat overcome by an increase in energy, but excessive energy consumption is not desirable for an implantable medical system. In embodiments, an electrode that is not significantly adversely affected by, for example, a coating is an electrode that has impedance properties that are not increased by more than about 15% of an electrode that is used for clinical purposes, such as for example, the helix tip electrode of Medtronic, Inc.'s SELECT-SECURE Model 3830 leads which is dip coated with BDP (no polymer).

As used herein, an electrode that is coated with a first composition is the "same or substantially similar" as (or to) an electrode coated with a different composition when the electrode coated with the different composition is of the same model and made by the same manufacture as the electrode coated with the first composition. For example, a helix tip electrode of, or for use in, a Medtronic, Inc. SELECT-SECURE Model 3830 lead that is coated with Biolinx is the same or substantially similar to a helix tip electrode of, or for use in, a Medtronic, Inc. SELECT-SECURE Model 3830 lead that is coated with BDP only (no polymer).

As used herein, reference to a particular therapeutic agent, such as BDP, refers to the therapeutic agent and salts, hydrates, isomers, and polymorphs thereof.

The specific Examples set forth herein below are intended to illustrate particular aspects of the disclosure and are not intended to limit the scope of the claims.

EXAMPLES

In the following examples, electrodes were coated with beclomethasone dipropionate ("BDP") alone, BDP in poly(trimethylene carbonate) ("PTMC"), BDP in poly(lactic-co-glycolic acid) ("PLGA"), or BDP in Biolinx® (Medtronic Vascular, Inc.). The coating uniformity and durability were evaluated. The elution profile of BDP was also evaluated. In addition, the effect of the coatings on electrode resistance was tested.

EXAMPLE 1

Coating Composition and Process

Titanium Nitride helix tip electrodes of Medtronic, Inc.'s SELECT-SECURE Model 3830 leads were coated as follows.

For BDP alone, BDP was dissolved in isopropyl alcohol to generate a saturated BDP solution. The saturated BDP solution was applied to the helix tip electrode of an assembled Model 3830 lead, and the isopropyl alcohol was allowed to evaporate. Alternatively, an approximate 0.2% BDP solution was prepared in acetone. The solution was then transferred to a syringe. Using Electro-Nano-Spray (ENS) process, the solution was forced into a nozzle and under pressure accelerated into an electrical field. In this electrical field, the solution was dispersed into droplets due to the their repulsive charges and the charges droplets were deposited on to the target (helix electrode).

For BDP-PTMC, a 20% BDP/80% PTMC composition was prepared as follows. Briefly, appropriate amounts of BDP and PTMC were dissolved in solvent (DCM/IPA=3:1 ratio) to make approximate 1% solution. The helix electrode of a Model 3830 lead was spray coated with approximately 110 micrograms of the BDP-PTMC via an ENS process as described above.

For BDP-PLGA, a 50% BDP/50% PLGA composition was prepared as follows. Briefly, appropriate amounts of BDP and PLGA were prepared in isopropyl alcohol to make approximate 1% solution. The helix electrode of a Model 3830 lead was spray coated with approximately 95 micrograms of the BDP-PLGA via an ENS process as described above.

For BDP-Biolinx®, a 20% BDP/80% Biolinx® composition was prepared as follows. Briefly, appropriate amounts of BDP and Biolinx polymer were dissolved in solvent (acetone/methanol=9:1 ratio) to make approximate 1% solution. The helix electrode of a Model 3830 lead was spray coated with approximately 135 micrograms of the BDP-Biolinx® via an ENS process as described above.

For each of the electrodes coated by an ENS process, the weight of the coatings applied to the electrode was determined as follows. Briefly, an uncoated helix electrode was weighed using an analytical balance. After the helix was coated with respective formulation and dried in a desiccator, the coated helix was then weighed. The difference between the two weight measurements was calculated as the coat weight. The relative standard deviation ("RSD") of the coating weight was determined (n=15 for the BDP alone (ENS) coating and n=35 for the rest of the coatings (with polymers) respectively). The results are presented in Table 1 below.

TABLE 1

| Polymer | Coat weight (micrograms) | % RSD (coat weight) |
|---|---|---|
| None - BDP alone (ENS) | 28.09 ± 1.58 | 5.63 |
| PLGA | 95 ± 4 | 4.00 |
| Biolinx | 134 ± 8 | 5.79 |
| PTMC | 111 ± 4 | 3.75 |

Coat weight

As shown in Table 1, the electo-nano-spray process resulted in fairly uniform coating-to-coating applications for each of listed polymers. It should be noted that the electonano-spray process has not yet been optimized for the particular BDP-polymer compositions, and it is believed that an optimized process will result in less RSD for each of the BDP-polymer compositions.

Visual and electron micrograph inspection of the coated electrodes revealed a more uniform coating of the electrode with the BDP-polymer compositions relative to the electrodes coated with BDP alone (data not shown).

EXAMPLE 2

Elution Profile

Figure 5:
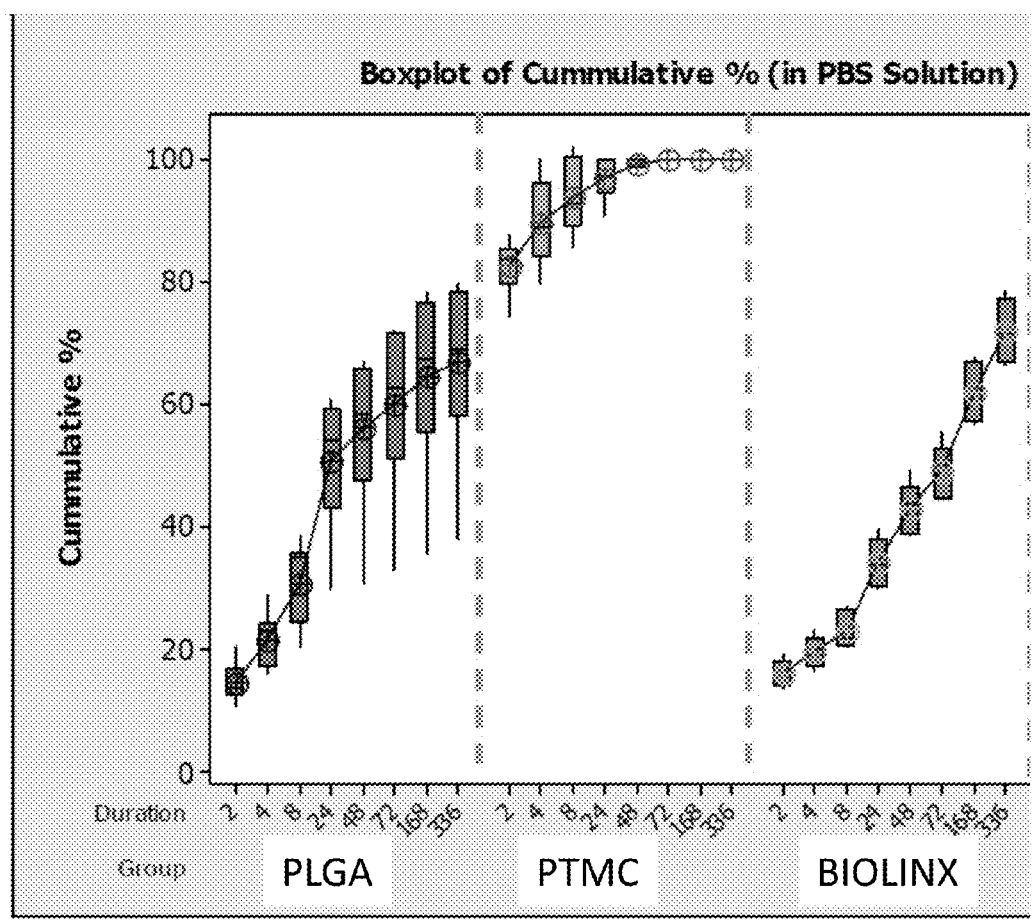
FIG. 5 is a graph of cumulative percent of beclomethasone dipropionate (BDP) released from various BDP-polymer coated electrodes over time.

Elution of BDP from electrodes coated as described in Example 1 above was evaluated as follows. Briefly, the coated electrodes were placed in a solution of phosphate buffered saline (PBS) with 5% sodium dodecyl sulfate (SDS), pH 7, at 37° C. for two weeks. At two, four, eight, 13, 48, 72, 169 and 336 hours after incubation of the coated electrode in the PBS/SDS, a 10 microliter aliquot was sampled and evaluated for BDP by using high performance liquid chromatography (HPLC) procedures. The elution profiles are depicted in FIG. 5 for electrodes coated with BDP-PLGA, BDP-PTMS and BDP-Biolinx® in terms of cumulative percent of BDP eluted over time.

Figure 6:
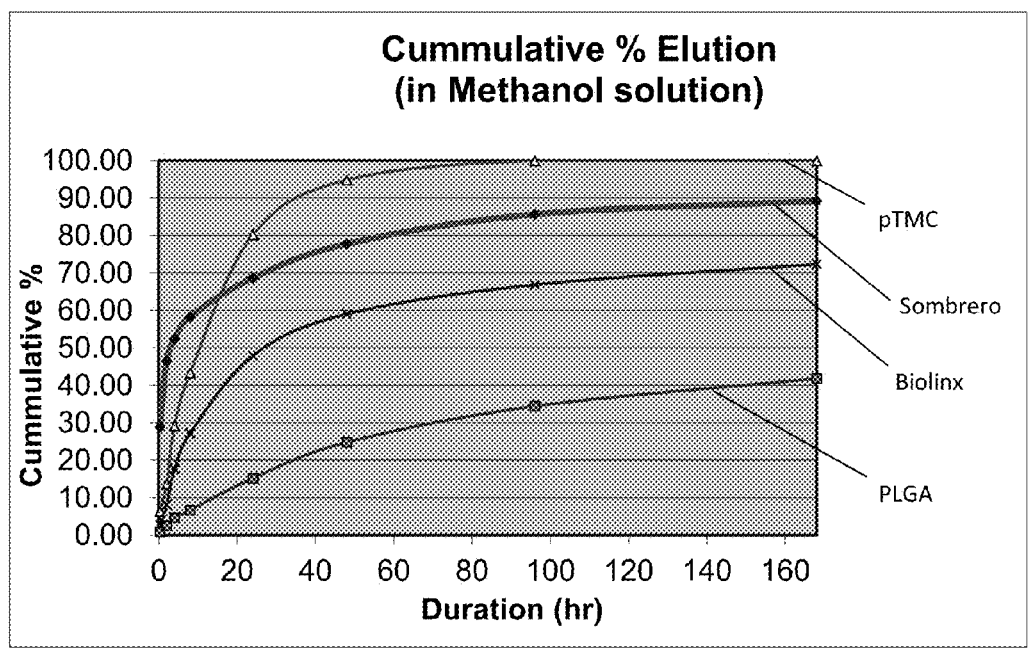
FIG. 6 is a graph of cumulative percent of beclomethasone dipropionate (BDP) released from various BDP-polymer coated electrodes over time.

As an alternative, electrodes coated with BDP-alone, BDP-PLGA, BDP-PTMC, or BDP-Biolinx® were placed in a 50/50 (v/v) methanol/water solution at room temperature for one week. At 0.24, 2, 4, 8, 24, 48, 96, and 168 hours aliquots were sampled and evaluated for BDP as described above. Elution profiles are depicted in FIG. 6. Total BDP assay (amount, based on the elution method at one week, 168 hours, and final extraction using methanol) is shown below in Table 2 for electrodes coated with BDP-polymer or BDP alone, along with the relative standard deviation ("RSD"). Results of testing from coating with three different lots of BDP are shown in Table 2. N=10 for each data from lot 1 to 3 respectively and N=6 for each data from ENS process (with or without polymers) in Table 2

TABLE 2

BDP elution profile - PBS/SDS

| Polymer | Elution Assay (micrograms) | % RSD (assay) |
| --- | --- | --- |
| None (BDP alone) - lot 1 | 20.06 ± 3.87 | 19.28 |
| None (BDP alone) - lot 2 | 19.00 ± 4.86 | 25.29 |
| None (BDP alone) - lot 3 | 17.57 ± 2.52 | 14.32 |
| None (BDP alone) - ENS | 25.25 ± 2.11 | 8.37 |
| PLGA | 45.9 ± 2.19 | 4.76 |
| Biolinx | 16.6 ± 0.86 | 5.20 |
| PTMC | 16.6 ± 0.8 | 4.79 |

As shown in FIG. 5, elution of BDP from PLGA and Biolinx® occurs slowly over time, while release of BDP from PTMC is more rapid with complete elution in about 2 days. Similar results are shown in FIG. 6, but with slower elution of BDP, particularly from PTMC. However, it is believed that PBS/SDS elution (FIG. 5) would more closely match physiological conditions than the 50/50 methanol/water elution (FIG. 6). In FIG. 6, the results for "Sombrero" are results for dip coated BDP-alone (without polymer).

It will be understood that release rates from Biolinx-like polymer compositions may be varied by adjusting the ratio of the three polymers (C19, C10, PVP) in the polymer blend, in modifying the constituents of the pendant groups of the C19 or C10 polymers, or the like.

In each case, elution of BDP from a polymer was substantially more consistent that elution without polymer (BDP alone). With the polymers, the RSD was about 5%, while without the polymers the RSD of dip coated BDP was about 20% (see Table 2). ENS coated BDP-alone electrodes exhibited a marked improvement over dip coated electrodes (about 8.4% RSD relative to about 20% RSD, respectively), but ENS coated BDP-alone was still not as reproducible as when coated with a polymer (see Table 2).

While each of PLGA, PTMC and Biolinx® may serve as a suitable vehicle for storage and elution of drugs, such as BDP (with PLGA and Biolinx® being more preferred for long-term release of hydrophobic drugs such as BDP), these polymer compositions were thought to be electrically insulating and thus not suitable for coating of an electrode. Accordingly, the electrical properties of electrodes coated with such polymers were tested.

EXAMPLE 3

Electrical Properties

Electrical impedance as a function of time in saline solution and the impedance-frequency scans of coated helix tip electrodes of Medtronic Model 3830 leads, which tip electrodes were coated as described above in Example 1, were tested in vitro. Briefly, the unipolar impedance of the coated electrode was measured between the coated electrode and the indifferent electrode in a salt solution tank at controlled temperature. The measurement was taken at the initial soak point and after approximately one, four and 24 hours. The impedance-frequency scans were carried over the frequency ranges from 0.1 Hz to 10,000 Hz in the saline solution tank.

Figure 7:
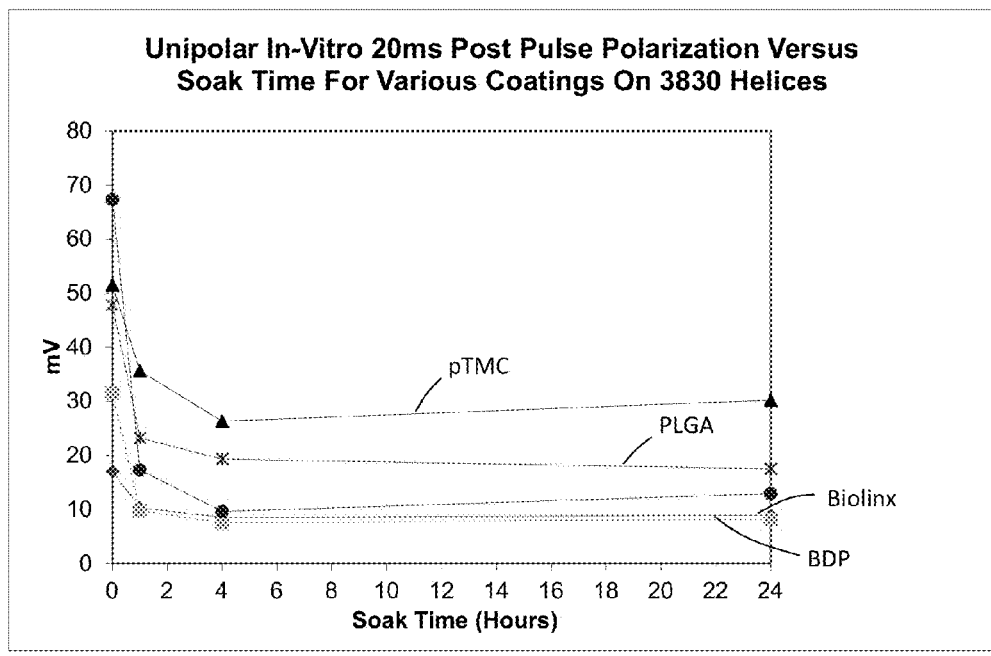
FIG. 7 is a graph of impedance over soak time for leads having helix tip electrodes coated with various BDP-polymers or BDP alone.
Figure 8:
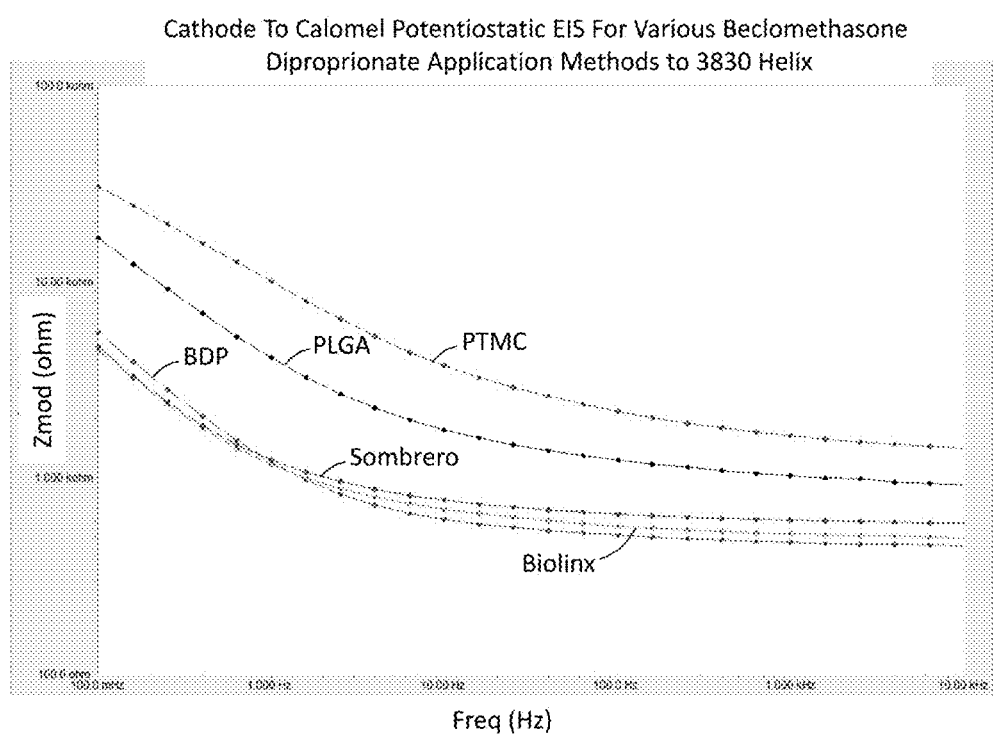
FIG. 8 is graph of impedance versus frequency for leads having helix tip electrodes coated with various BDP-polymers or BDP alone The schematic drawings are not necessarily to scale. Like numbers used in the figures refer to like components, steps and the like. However, it will be understood that the use of a number to refer to a component in a given figure is not intended to limit the component in another figure labeled

Results are presented in FIGS. 7-8. In FIG. 7, the resistance relative to soak time is displayed. In FIG. 8, impedance vs. frequency is shown.

As shown in FIGS. 7-8, the leads having the distal tip helix electrode coated with BDP-alone, either by dip coating or ENS coating, produced similar impedance values, which would be expected to be similar to uncoated electrodes. With longer soak times (see FIG. 7), it would be expected that most of the BDP would have eluted from the surface of the electrode when no polymer is present.

The results presented in FIGS. 7-8 also show that a substantial increase (relative to electrodes with no polymer coating) in impedance is detected with PTMC and PLGA coated electrodes. Such an effect is not surprising due to the presumed electrical insulating properties of these polymers. While the increase in impedance, particularly with the PLGA, may not be sufficiently great to prevent its use in coating an implantable electrode, it would be expected that significantly more energy would be needed to produce a desired physiological effect with such coated electrodes than with electrodes that either do not have a coating or that are coated with a drug such as BDP.

Surprisingly, the electrodes coated with BDP-Biolinx® had similar, and even slightly lower, impedance than those coated with BDP alone. Accordingly, the Biolinx® coated electrodes are desirable not only from a drug-release and processing perspective, but also from an electrical property perspective. The use of Biolinx® to coat electrodes, as shown herein, should not significantly adversely affect, and may actually improve, the electrical characteristics of the electrode.

The results presented herein with regard to BDP-Biolinx® coated electrodes should be applicable to any drug- Biolinx® coated electrode. Further, the results presented herein should also be applicable to Biolinx-like polymer blends that have varying amounts of each polymer (C19, C10, PVP) or that have modifications to the pendant moieties of the C19 and C10 polymers.

Thus, embodiments of DRUG-ELUTING POLYMER-COATED IMPLANTABLE ELECTRODE are disclosed. One skilled in the art will appreciate that the electrodes, leads, devices, systems and methods described herein can be practiced with embodiments other than those disclosed. The disclosed embodiments are presented for purposes of illustration and not limitation. One will also understand that components of the leads depicted and described with regard the figures and embodiments herein may be interchangeable.

What is claimed is:

1. An implantable medical lead comprising:
   an electrode configured to contact tissue when implanted;
   a contact electrically coupled to the electrode, wherein the contact is configured to electrically couple the lead to a medical device; and
   a coating on the electrode, the coating comprising:
      (A) a polymer composition that includes
         (i) a terpolymer formed from monomer subunits consisting essentially of vinyl acetate, alkyl methyl acrylate and n-vinyl pyrrolidone;
         (ii) a copolymer formed from monomer subunits consisting essentially of vinyl acetate and alkyl methacrylate; and
         (iii) polyvinyl pyrrolidone; and
      (B) optionally, one or more therapeutic agents,
   wherein the coating is otherwise free from electrically conductive material and does not substantially adversely affect impedance properties of the electrode.

2. The implantable medical lead of claim 1, wherein the polymer composition comprises from about 60 to about 70 weight percent of the terpolymer, from about 20 to about 30 weight percent of the copolymer, and from about 5 to about 15 weigh percent of the polyvinyl pyrrolidone.

3. The implantable medical lead of claim 1, wherein the polymer composition comprises about 63 weight percent of the terpolymer, about 27 weight percent of the copolymer, and about 10 weight percent of the polyvinyl pyrrolidone.

4. The implantable medical lead of claim 1, wherein the relative mole percent of the monomer subunits of the terpolymer comprises from about 2% to about 30% vinyl acetate, from about 40% to about 77% alkyl methyl acrylate, and from about 15% to about 30% n-vinyl pyrrolidone.

5. The implantable medical lead of claim 1, wherein the relative mole percent of the monomer subunits of the copolymer comprises from about 2% to about 70% vinyl acetate and from about 30% to about 97% alkyl methyl acrylate.

6. The implantable medical lead of claim 1, wherein the alkyl methacrylate of the terpolymer and the alkyl methacrylate of the copolymer are independently selected from the group consisting of methyl methacrylate, ethyl methacrylate, propyl methacrylate, butyl methacrylate, pentyl methacrylate, and hexyl methacrylate.

7. The implantable medical lead of claim 1, wherein the alkyl methacrylate of the terpolymer is n-hexyl methacrylate and wherein the alkyl methacrylate of the copolymer is n-butyl methacrylate.

8. The implantable medical lead of claim 1, wherein the coating further comprises a therapeutic agent(s).

9. The implantable medical lead of claim 8, wherein the one or more therapeutic agents comprises a therapeutic agent is selected from the group consisting of an anti-inflammatory agent and an antimicrobial agent.

10. The implantable medical lead of claim 8, wherein the one or more therapeutic agents comprise an anti-inflammatory agent.

11. The implantable medical lead of claim 8, wherein the one or more therapeutic agents comprise a steroid.

12. The implantable medical lead of claim 8, wherein the one or more therapeutic agents comprise beclomethasone or a pharmaceutically acceptable salt thereof.

13. The implantable medical lead of claim 8, wherein the one or more therapeutic agent agents comprise beclomethasone dipropionate.

14. The implantable medical lead of claim 1, wherein the electrode is a helix electrode.

15. The implantable medical lead of claim 1, wherein the coating does not increase the impedance of the electrode more than 10% relative to the same electrode coated with beclomethasone dipropionate alone.

16. The implantable medical lead of claim 1, wherein the coating decreases the impedance of the electrode relative to an uncoated electrode.

17. A system comprising:
   an implantable medical lead according to claim 1; and
   a medical device to which the lead is configured to operably couple.

18. A method comprising:
   coating an electrode with a polymer composition comprising (i) a terpolymer formed from monomer subunits consisting essentially of vinyl acetate, alkyl methyl acrylate and n-vinyl pyrrolidone; (ii) a copolymer formed from monomer subunits consisting essentially of vinyl acetate and alkyl methacrylate; and (iii) polyvinyl pyrrolidone; and (B) optionally, one or more therapeutic agents, wherein the coating is otherwise free form electrically conductive material and does not substantially adversely affect impedance properties of the electrode; and
   incorporating the coated electrode into an implantable medical lead during assembly of the lead.

19. The method of claim 18, wherein coating the electrode comprises electro-nano-spraying the electrode with the polymer composition.

20. The method of claim 18, wherein the coating composition comprises the one or more therapeutic agents.

* * * * *

UNITED STATES PATENT AND TRADEMARK OFFICE
CERTIFICATE OF CORRECTION

PATENT NO. : 9,682,229 B2
APPLICATION NO. : 13/537249
DATED : June 20, 2017
INVENTOR(S) : Paul H. Wu, Catherine E. Taylor and Terrell M. Williams It is certified that error appears in the above-identified patent and that said Letters Patent is hereby corrected as shown below:

In the Claims

Column 16, Claim 8, Lines 7-8: Replace "The implantable medical lead of claim 1, wherein the coating further comprises a therapeutic agent(s)" with --The implantable medical lead of claim 1, wherein the coating comprises the one or more the therapeutic agents.--

Column 16, Claim 19, Lines 51-53: Replace "The method of claim 18, wherein coating the electrode comprises electro-nano-spraying the electrode with the polymer composition" with --The method of claim 18, wherein coating the electrode comprises electro-nano-spraying the electrode with the composition.--

Signed and Sealed this
Twenty-fourth Day of October, 2017

Joseph Matal
*Performing the Functions and Duties of the
Under Secretary of Commerce for Intellectual Property and
Director of the United States Patent and Trademark Office*